(12) United States Patent
Johnson et al.

(10) Patent No.: US 9,932,315 B2
(45) Date of Patent: Apr. 3, 2018

(54) PERSISTENT CARBENE ADDUCTS AND RELATED METHODS

(71) Applicant: Massachusetts Institute of Technology, Cambridge, MA (US)

(72) Inventors: Jeremiah A. Johnson, Boston, MA (US); Aleksandr V. Zhukhovitskiy, El Cerrito, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/502,678

(22) PCT Filed: Aug. 7, 2015

(86) PCT No.: PCT/US2015/044295
§ 371 (c)(1),
(2) Date: Feb. 8, 2017

(87) PCT Pub. No.: WO2016/022965
PCT Pub. Date: Feb. 11, 2016

(65) Prior Publication Data
US 2017/0233349 A1   Aug. 17, 2017

Related U.S. Application Data

(60) Provisional application No. 62/035,371, filed on Aug. 8, 2014.

(51) Int. Cl.
C07D 233/16 (2006.01)

(52) U.S. Cl.
CPC ................ *C07D 233/16* (2013.01)

(58) Field of Classification Search
CPC .................................................. C07D 233/16
See application file for complete search history.

(56) References Cited

U.S. PATENT DOCUMENTS

| | | |
|---|---|---|
| 3,301,895 A | 1/1967 | Sayigh et al. |
| 6,395,916 B1 | 5/2002 | Buchwald et al. |
| 6,426,419 B1 | 7/2002 | Grubbs et al. |
| 6,610,626 B2 | 8/2003 | Grubbs et al. |
| RE38,676 E | 12/2004 | Grubbs et al. |
| 6,838,489 B2 | 1/2005 | Bell et al. |
| 7,041,758 B2 | 5/2006 | Goodall et al. |
| 7,439,395 B2 | 10/2008 | Ignatyev et al. |
| 7,560,582 B2 | 7/2009 | Buchwald et al. |
| 8,168,830 B2 | 5/2012 | Armstrong et al. |
| 8,481,722 B2 | 7/2013 | Armstrong et al. |
| 9,382,210 B2 | 7/2016 | Johnson et al. |
| 2008/0258113 A1 | 10/2008 | Clyburne et al. |
| 2016/0272623 A1 | 9/2016 | Johnson et al. |
| 2016/0289248 A1 | 10/2016 | Johnson et al. |
| 2016/0355484 A1 | 12/2016 | Johnson et al. |

FOREIGN PATENT DOCUMENTS

| | | |
|---|---|---|
| WO | WO 00/071554 A2 | 11/2000 |
| WO | WO 02/076613 A1 | 10/2002 |
| WO | WO 2008/069688 A2 | 6/2008 |
| WO | WO 2012/002913 A1 | 1/2012 |

OTHER PUBLICATIONS

International Search Report and Written Opinion for PCT/US15/44295 dated Nov. 13, 2015.
International Preliminary Report on Patentability for PCT/US15/44295 dtaed Feb. 23, 2017.
Kuchenbeiser, Reactivity of Bis(amino)cyclopropenylidenes (BACs) and Cyclic(alkyl)(amino)carbenes (CAACs). UC Riverside Electronic Theses and Dissertations. Aug. 2009 217 pages. Last accessed on Apr. 20, 2017 at <http://escholarship.org/uc/item/6h67q1f4>.
Dyker et al., Soluble Allotropes of Main-Group Elements. Science. Aug. 22, 2008;321(5892):1050-1.
Kuhn et al., A Facile Preparation of Imidazolinium Chlorides. Org. Lett. 2008;10(10):2075-7. Epub Apr. 16, 2008.
Kuhn et al., 1,3-Diisopropyl-4,5-dimethylimidazolium-2-N,N'-diisopropylamidinat, ein neuartiges Betain. Zeitschrift Für Naturforschung B. Apr. 1999;54(4):434-40.
Leuthamer et al., π-Face Donor Properties of N-Heterocyclic Carbenes in Grubbs II Complexes. Chem. Eur. J. 2008 Jun. 20;14(18):5465-81. Epub May 6, 2008.
MacLeod et al., PEGylated N-Heterocyclic Carbene Anchors Designed to Stabilize Gold Nanoparticles in Biologically Relevant Media. J. Am. Chem. Soc. 2015;137(25):7974-7. Epub Jun. 17, 2015.
Masuda et al., Stable P-Heterocyclic Carbenes: Scope and Limitations. Chem. Asian J. Jan. 8, 2007;2(1):178-87. Epub Nov. 8, 2006.
Scholl et al., Synthesis and Activity of a New Generation of Ruthenium-Based Olefin Metathesis Catalysts Coordinated with 1,3-Dimesityl-4,5-dihydroimidazol-2-ylidene Ligands. Org. Lett. 1999;1(6):953-6. Epub Aug. 13, 1999.
Takamizawa et al., Addition reactions of thiazolium ylids with arylisothiocyanates and di-p-tolylcarbodiimide. Novel zwitter-ionic compounds stabilized by nitrogen and sulfur. Tetrahedron Letters. 1968;9(37):4027-30.
Takamizawa et al., Syntheses of 4-Aryliminoparabanic Acids and 2-Arylimino-2,3-dihydro-1,4-thiazine Derivatives vis 2-N,N'-Diarylamidinothiazolium Salts. Chem. Pharm. Bull. 1974;22:311-5.
Türkmen et al., 1,3-Diarylimidazolidin-2-ylidene (NHC) complexes of Pd(II): Electronic effects on cross-coupling reactions and thermal decompositions. J. Organomet. Chem. Sep. 1, 2006;691(18):3749-59. Epub May 20, 2006.

(Continued)

*Primary Examiner* — Michael Barker
(74) *Attorney, Agent, or Firm* — Wolf, Greenfield & Sacks, P.C.

(57) ABSTRACT

Persistent carbene adducts and methods of forming the same are generally described, as well as compositions comprising the persistent carbene adduct. In some embodiments, methods are provided comprising heating a persistent carbene to relatively high temperatures to convert the persistent carbene into a persistent carbene-carbodiimide adduct. In certain embodiments, the percent of the persistent carbene that is converted to the persistent carbene-carbodiimide adduct is relatively high (e.g., at least about 50%). In some embodiments, the persistent carbene-carbodiimide adducts formed via the methods described herein may be relatively stable. Compositions comprising the persistent carbene-carbodiimide adducts of the present invention may be useful for applications involving catalysis, organometallic chemistry, sensing, and surface functionalization, amongst others.

18 Claims, 4 Drawing Sheets

(56) References Cited

OTHER PUBLICATIONS

Zhukhovitskiy et al., Addressable Carbene Anchors for Gold Surfaces. J. Am. Chem. Soc. 2013;135(20):7418-21. Epub May 13, 2013.

Zhukhovitskiy et al., Carbene Ligands in Surface Chemistry: From Stabilization of Discrete Elemental Allotropes to Modification of Nanoscale and Bulk Substrates. Chem. Rev. 2015;115(20):11503-32. Epub Sep. 22, 2015.

Zhukhovitskiy et al., Cycloelimination of Imidazolidin-2-ylidene N-Heterocyclic Carbenes: Mechanism and Insights into the Synthesis of Stable "NHC-CDI" Amidinates. Chem. Eur. J. Feb. 20, 2015;21(15):5685-8. Supporting Information Included.

PERSISTENT CARBENE ADDUCTS AND RELATED METHODS

RELATED APPLICATIONS

The present application is a National Stage Application under 35 U.S.C. § 371 of International Application Serial No. PCT/US2015/044295, filed Aug. 7, 2015, entitled "PERSISTENT CARBENE ADDUCTS AND RELATED METHODS," which claims priority under 35 U.S.C. § 119(e) to U.S. provisional application, U.S. Ser. No. 62/035,371, filed Aug. 8, 2014, entitled "PERSISTENT CARBENE ADDUCTS AND RELATED METHODS," each of which is incorporated herein by reference in their entirety for all purposes.

TECHNICAL FIELD

Persistent carbene adducts and methods of forming the same are provided.

BACKGROUND

Though the existence of carbenes has been known for over a century, persistent carbenes have only recently been discovered. Traditionally, carbenes were believed to be short-lived and/or non-isolatable due to the electron-deficient and ambiphilic nature of many carbenes, which rendered them highly reactive and difficult to isolate. Recently, it was found that carbenes can be stabilized via conjugation with appropriate heteroatoms. This landmark discovery led to the first isolation of heterocyclic carbenes, and spawned interest in new synthetic approaches involving persistent carbenes. Synthetic approaches often utilize persistent carbene adducts, which have been used to successfully synthesize organometallic catalysts, components of novel polymers, and efficient organocatalysts. While several persistent carbene adducts exist, more persistent carbene adducts and methods of forming persistent carbene adducts are needed.

SUMMARY

Persistent carbene adducts and methods of forming the same are provided, as well as compositions comprising the persistent carbene adducts. The subject matter of the present invention involves, in some cases, interrelated products, alternative solutions to a particular problem, and/or a plurality of different uses of one or more systems and/or articles.

In one set of embodiments, compounds are provided. In some embodiments, a compound comprises the structure:

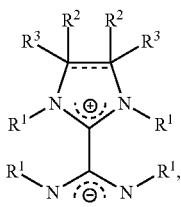

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile, provided at least two $R^1$ are optionally substituted aryl;
each $R^2$ and $R^3$ are the same or different and are absent, hydrogen, optionally substituted alkyl, optionally substituted heteroalkyl, halo, optionally substituted acyl, or optionally substituted phosphine;
===== is a single or double bond, provided when ===== is a double bond, each $R^3$ is absent. In another set of embodiments, methods are provided. In some embodiments, a method for forming a compound comprising the structure:

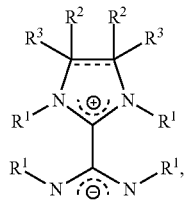

or a tautomer thereof, comprises the step of heating a precursor compound to a temperature of about 80° C. or greater, wherein the percent conversion to the compound is greater than or equal to 50%, and wherein the precursor compound has the structure:

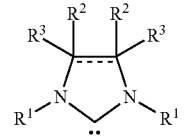

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile, provided at least two $R^1$ are optionally substituted aryl;
each $R^2$ and $R^3$ are the same or different and are absent, hydrogen, optionally substituted alkyl, optionally substituted heteroalkyl, halo, optionally substituted acyl, or optionally substituted phosphine; and
===== is a single or double bond, provided when ===== is a double bond, each $R^3$ is absent.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1B shows crystal structures of N-heterocyclic-carbodiimide adducts, according to certain embodiments.

FIG. 1C shows crystal structures of N-heterocyclic-carbodiimide adducts, according to certain embodiments.

DETAILED DESCRIPTION

Figure 1:
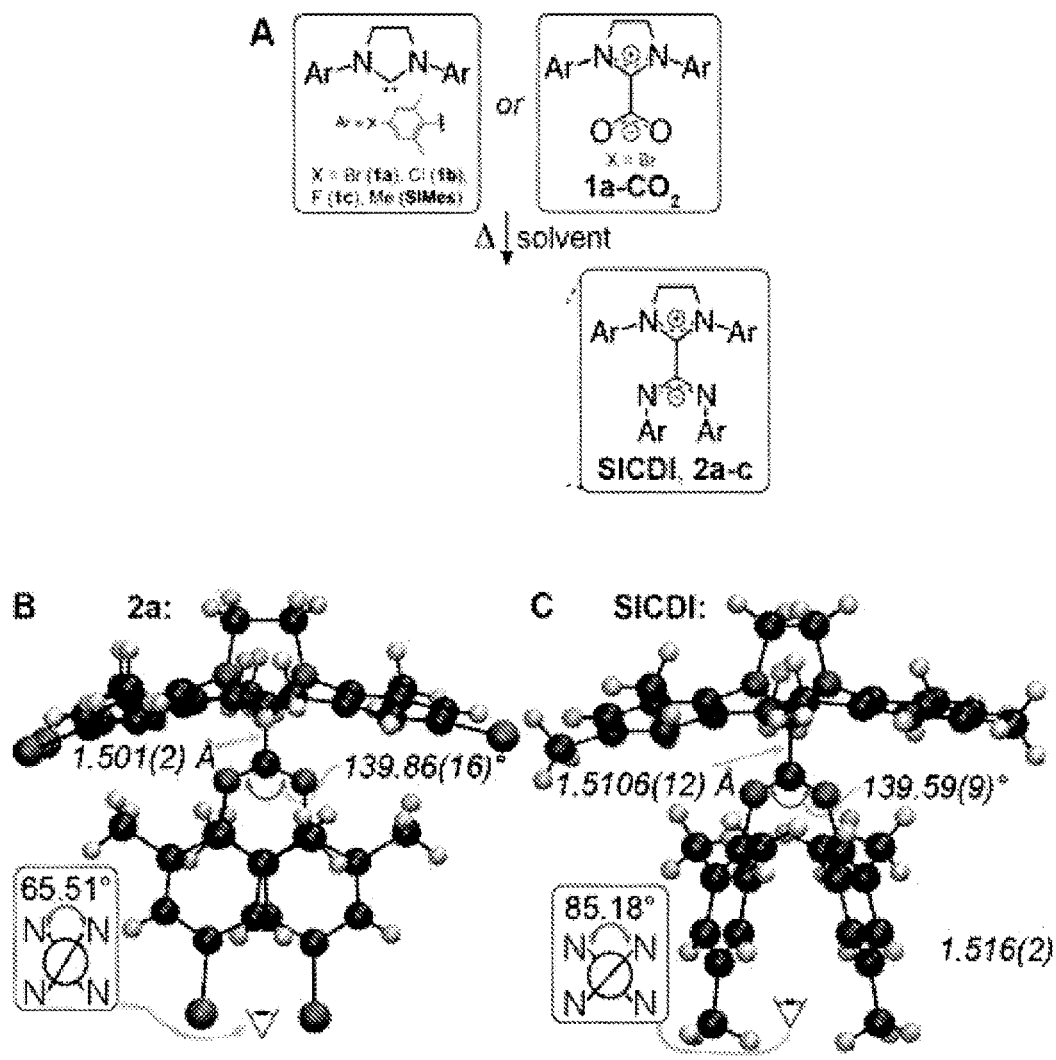
FIG. 1 shows a reaction scheme of the transformation of N-heterocyclic carbenes and N-heterocyclic carbene-$CO_2$ adducts to N-heterocyclic-carbodiimide adducts, according to certain embodiments.

Persistent carbene adducts and methods of forming the same are generally described, as well as compositions comprising the persistent carbene adduct. In some embodiments, methods are provided comprising heating a persistent carbene to relatively high temperatures to convert the persistent carbene into a persistent carbene-carbodiimide adduct. In certain embodiments, the percent of the persistent carbene that is converted to the persistent carbene-carbodiimide adduct is relatively high (e.g., at least about 50%). In some embodiments, the persistent carbene-carbodiimide adducts formed via the methods described herein may be relatively stable. Compositions comprising the persistent carbene-carbodiimide adducts of the present invention may be useful for applications involving catalysis, organometallic chemistry, sensing, and surface functionalization, amongst others.

In one aspect, compositions comprising persistent carbene adducts are provided. In some embodiments, the persistent carbene adduct may be an N-heterocyclic carbene-carbodiimide adduct. In some such embodiments, the N-heterocyclic carbene adduct comprises Formula (I):

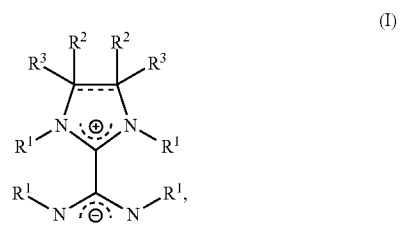

or a tautomer thereof, wherein:

each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile;

each $R^2$ and $R^3$ are the same or different and are absent, hydrogen, optionally substituted alkyl, optionally substituted heteroalkyl, halo, optionally substituted acyl, or optionally substituted phosphine; and ===== is a single or double bond, provided when ===== is a double bond, each $R^3$ is absent. In certain embodiments, ===== is a single bond. In some embodiments, each $R^2$ and $R^3$ are the same or different and are hydrogen or optionally substituted alkyl and ===== is a single bond. In certain embodiments, each $R^2$ and $R^3$ is hydrogen and ===== is a single bond.

In some embodiments, for a compound of Formula (I) (or tautomer thereof), at least one $R^1$ is not optionally substituted alkyl. In some instance, at least two $R^1$ are not optionally substituted alkyl. In certain instances, at least three $R^1$ are not optionally substituted alkyl. In certain embodiments, for a compound of Formula (I) (or tautomer thereof), each $R^1$ is the same or different and are hydrogen, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile.

In some embodiments, for a compound of Formula (I) (or tautomer thereof), each $R^1$ is the same or different and are hydrogen, optionally substituted alkyl, optionally substituted heteroalkyl, optionally substituted cycloheteroalkyl, optionally substituted alkenyl, optionally substituted alkynyl, optionally substituted aryl, or optionally substituted heteroaryl. In certain embodiments, each $R^1$ is the same or different and are optionally substituted cycloalkyl, optionally substituted cycloheteroalkyl, optionally substituted cycloalkenyl, optionally substituted aryl, or optionally substituted heteroaryl. In some instances, each $R^1$ is the same or different and are optionally substituted aryl or optionally substituted heteroaryl.

In some embodiments, at least two $R^1$ are the same. In certain embodiments, for a compound of Formula (I) (or tautomer thereof), each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile, provided at least two $R^1$ are the same. For instance, in some embodiments, at least two $R^1$ are optionally substituted aryl or optionally substituted heteroaryl. In certain embodiments, at least three $R^1$ are the same. In some instances, for a compound of Formula (I) (or tautomers thereof), each $R^1$ is the same.

In some embodiments, at least one $R^1$ is an optionally substituted unsaturated moiety. In some instances, at least two $R^1$ are the same or different and are an optionally substituted unsaturated moiety. In certain cases, at least three $R^1$ are the same or different and are an optionally substituted unsaturated moiety. In certain embodiments, each $R^1$ is the same or different and is an optionally substituted unsaturated moiety. Non-limiting examples of optionally substituted unsaturated moieties include optionally substituted alkenyl, optionally substituted alkynyl, optionally substituted aryl, and optionally substituted heteroaryl. In some embodiments, the optionally substituted unsaturated moiety is optionally substituted aryl, and optionally substituted heteroaryl, or optionally substituted alkenyl.

In some embodiments, at least one $R^1$ is optionally substituted aryl. In some instances, at least two $R^1$ are the same or different and are optionally substituted aryl. In certain cases, at least three $R^1$ are the same or different and are optionally substituted aryl. In certain embodiments, each $R^1$ is the same or different and is optionally substituted aryl. In some embodiments, in which one or more $R^1$ (e.g., two $R^1$, three $R^1$, all $R^1$) are the same or different and are optionally substituted aryl, $R^1$ comprises the structure:

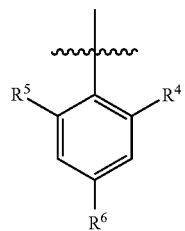

wherein $R^4$, $R^5$, and $R^6$ are same or different and are hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocyanate, or nitrile. In some such embodiments, $R^4$, $R^5$, and $R^6$ are the same or different and are halide, optionally substituted alkyl, or optionally substituted aryl. In some embodiments, $R^4$ and $R^5$ are optionally substituted alkyl and $R^6$ is halide. In some embodiments, $R^4$ and $R^5$ are optionally substituted alkyl and $R^6$ is F, Cl, or Br. In some embodiments, $R^4$, $R^5$, and $R^6$ are the same or different and optionally substituted alkyl. In some embodiments, $R^4$, $R^5$, and $R^6$ are methyl.

In some embodiment, the compound of Formula (I) has the structure:

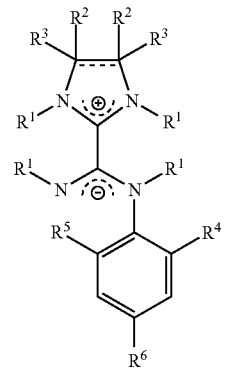

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile;
each $R^2$ and $R^3$ are the same or different and are absent, hydrogen, optionally substituted alkyl, optionally substituted heteroalkyl, halo, optionally substituted acyl, or optionally substituted phosphine;
$R^4$, $R^5$, and $R^6$ are same or different and are hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocyanate, or nitrile; and
===== is a single or double bond, provided when ===== is a double bond, each $R^3$ is absent. In certain embodiments, $R^4$, $R^5$, and $R^6$ are the same or different and are halide, optionally substituted alkyl, or optionally substituted aryl. In some embodiments, each $R^2$ and $R^3$ are the same or different and are hydrogen or optionally substituted alkyl and ===== is a single bond. In certain embodiments, each $R^2$ and $R^3$ is hydrogen and ===== is a single bond.

In some embodiments, at least two $R^1$ are optionally substituted aryl, such that the compound of Formula (I) has the structure:

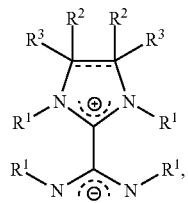

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile, provided at least two $R^1$ are optionally substituted aryl;
each $R^2$ and $R^3$ are the same or different and are absent, hydrogen, optionally substituted alkyl, optionally substituted heteroalkyl, halo, optionally substituted acyl, or optionally substituted phosphine; and
===== is a single or double bond, provided when ===== is a double bond, each $R^3$ is absent. In some such embodiments, at least one $R^1$ is not optionally substituted alkyl. For instance, $R^1$ may not be optionally substituted alkyl. In some embodiments, each $R^2$ and $R^3$ are the same or different and are hydrogen or optionally substituted alkyl and ===== is a single bond. In certain embodiments, each $R^2$ and $R^3$ is hydrogen and ===== is a single bond.

In some embodiments, the compound of Formula (I) has the structure:

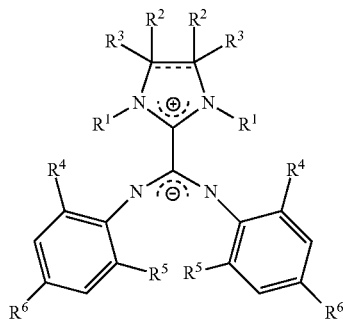

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile;
each $R^2$ and $R^3$ are the same or different and are absent, hydrogen, optionally substituted alkyl, optionally substituted heteroalkyl, halo, optionally substituted acyl, or optionally substituted phosphine;
$R^4$, $R^5$, and $R^6$ are same or different and are hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocyanate, or nitrile; and
===== is a single or double bond, provided when ===== is a double bond, each $R^3$ is absent. In certain embodiments, $R^4$, $R^5$, and $R^6$ are the same or different and are halide, optionally substituted alkyl, or optionally substituted aryl. In some embodiments, each $R^2$ and $R^3$ are the same or different and are hydrogen or optionally substituted alkyl and ===== is a single bond. In certain embodiments, each $R^2$ and $R^3$ is hydrogen and ===== is a single bond.

In some embodiments, the compound of Formula (I) has the structure:

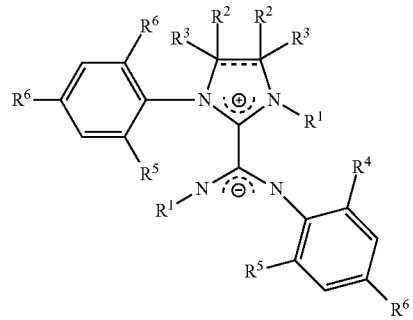

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile;
each $R^2$ and $R^3$ are the same or different and are absent, hydrogen, optionally substituted alkyl, optionally substituted heteroalkyl, halo, optionally substituted acyl, or optionally substituted phosphine;
each $R^4$, $R^5$, and $R^6$ are same or different and are hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocyanate, or nitrile; and
===== is a single or double bond, provided when ===== is a double bond, each $R^3$ is absent. In certain embodiments, each $R^4$, $R^5$, and $R^6$ are the same or different and are halide, optionally substituted alkyl, or optionally substituted aryl. In some embodiments, each $R^2$ and $R^3$ are the same or different and are hydrogen or optionally substituted alkyl and ===== is a single bond. In certain embodiments, each $R^2$ and $R^3$ is hydrogen and ===== is a single bond.

In some embodiments, the compound of Formula (I) has the structure:

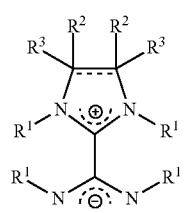

or a tautomer thereof, wherein:
each $R^1$ comprises the structure:

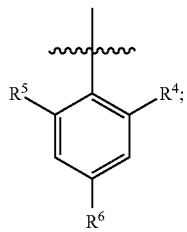

$R^2$ and $R^3$ are hydrogen, optionally substituted alkyl, optionally substituted heteroalkyl, halo, optionally substituted acyl, or optionally substituted phosphine;
each $R^4$, $R^5$, and $R^6$ are same or different and are hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocyanate, or nitrile; and
------ is a single bond. In some such embodiments, $R^2$ and $R^3$ are hydrogen or optionally substituted alkyl and each $R^4$, $R^5$, and $R^6$ are the same or different and are halide, optionally substituted alkyl, or optionally substituted aryl. In some such embodiments, $R^2$ and $R^3$ are hydrogen or optionally substituted alkyl and each $R^4$, $R^5$, and $R^6$ are the same or different and are halide or optionally substituted alkyl. In certain embodiments, $R^2$ and $R^3$ are hydrogen.

In some embodiments, the compound of Formula (I) has the structure:

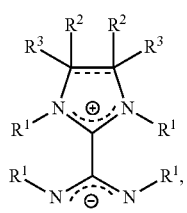

or a tautomer thereof, wherein:

each $R^1$ comprises the structure:

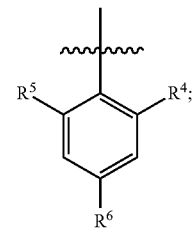

$R^2$ and $R^3$ are hydrogen, optionally substituted alkyl, or optionally substituted heteroalkyl;
each $R^4$ and $R^5$ are optionally substituted alkyl;
$R^6$ is halo; and
------ is a single bond. In some cases, $R^2$ and $R^3$ are hydrogen or optionally substituted alkyl. In certain cases, $R^2$ and $R^3$ are hydrogen. In certain embodiments, each $R^4$ and $R^5$ are $C_{1-6}$ alkyl (e.g., methyl).

In another aspect, methods for forming compounds of Formula (I) (or tautomers thereof) are provided. In some embodiments, a method for forming a compound of Formula (I):

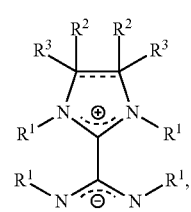

or a tautomer thereof, comprises the step of heating a precursor compound to a temperature of about 80° C. or greater, wherein the percent conversion to the compound is greater than or equal to 50%, and wherein the precursor compound has the structure:

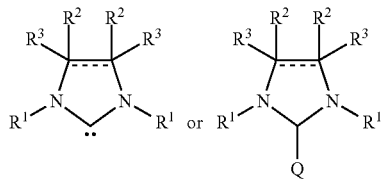

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile;
each $R^2$ and $R^3$ are the same or different and are absent, hydrogen, optionally substituted alkyl, optionally substituted heteroalkyl, halo, optionally substituted acyl, or optionally substituted phosphine;

------ is a single or double bond, provided when ------ is a double bond, each $R^3$ is absent; and Q is a thermolabile or photolabile protecting group. In some embodiments, $R^1$, $R^2$, and $R^3$ may be as described above with respect to a compound of Formula (I) or variation thereof. For example, in some embodiments, each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile, provided at least two $R^1$ are the same. As another example, in some embodiments, each $R^1$ is optionally substituted aryl.

In some embodiments, the precursor compound comprises the structure:

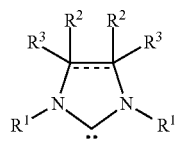

or a tautomer thereof, wherein:

each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile;

each $R^2$ and $R^3$ are the same or different and are absent, hydrogen, optionally substituted alkyl, optionally substituted heteroalkyl, halo, optionally substituted acyl, or optionally substituted phosphine; and ------ is a single or double bond, provided when ------ is a double bond, each $R^3$ is absent. In some embodiments, $R^1$, $R^2$, and $R^3$ may be as described above with respect to a compound of Formula (I).

In other embodiments, the precursor compound comprises the structure:

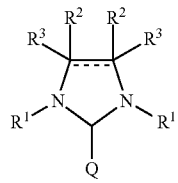

or a tautomer thereof, wherein:

each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile;

each $R^2$ and $R^3$ are the same or different and are absent, hydrogen, optionally substituted alkyl, optionally substituted heteroalkyl, halo, optionally substituted acyl, or optionally substituted phosphine;

------ is a single or double bond, provided when ------ is a double bond, each $R^3$ is absent; and Q is a thermolabile or photolabile protecting group. In some embodiments, $R^1$, $R^2$, and $R^3$ may be as described above with respect to a compound of Formula (I). Those of ordinary skill in the art would be knowledgeable of suitable thermolabile or photolabile protecting group. In some embodiments, Q is selected from the group consisting $-CO_2$, $-CCl_3$, $-SiCl_4$, -fluoroaryl, $-H$, $-CH_2CN$, $-OR'$, $-PR''_3$, $-PR''$, and $BR''_3$, where R' is optionally substituted alkyl or optionally substituted aryl and R" is hydrogen, optionally substituted alkyl, optionally substituted heteroalkyl, optionally substituted aryl, optionally substituted heteroaryl, optionally substituted halo, optionally substituted alkoxy, or optionally substituted amino. Other examples of possible protecting groups include thermolabile or photolabile carbenes and metals or metalloids. In some embodiments, the protecting group is $-CO_2$. It should be understood, in certain embodiments, one or more substituents on the persistent carbene may be eliminated with Q. Non-limiting examples include the following where | indicates the carbene carbon: H—|—$CCl_3$, H-|-fluoroaryl, F-|-fluoroaryl, H—|—$PR''_3$, H—|—$CH_2CN$, and H—|—OR'.

Figure 2:
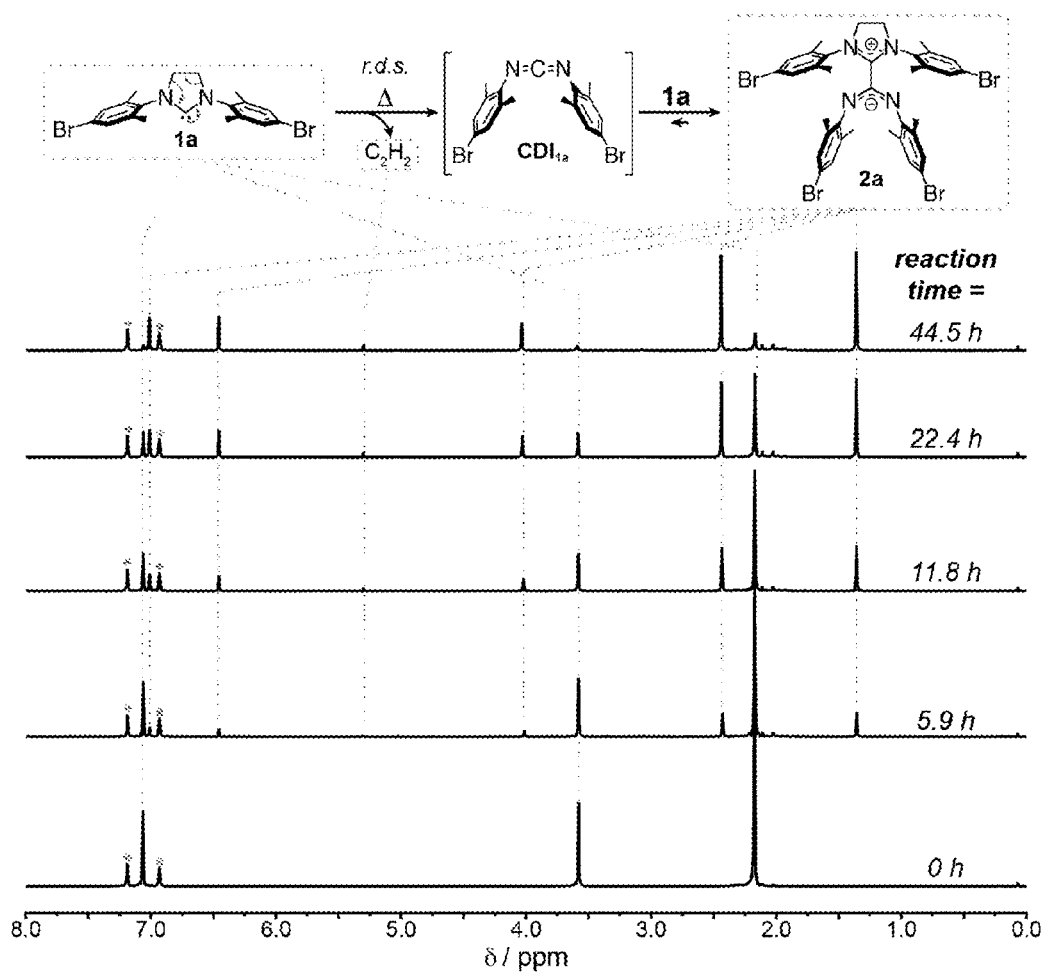
FIG. 2 shows a potential mechanism for the transformation of the N-heterocyclic carbene into the N-heterocyclic-carbodiimide and ethylene and $^1H$ NMR spectrum as a function of reaction time, according to certain embodiments.

Without being bound by theory, it is believed that heating the precursor compound to a relatively high temperature (e.g., at least 80° C., at least 100° C.) causes the precursor compound to undergo a cycloelimination reaction (e.g., a first order [3+2]-cycloelimination reaction) forming a carbodiimide and a byproduct derived from the precursor compound. For instance, the cycloelimination reaction may form:

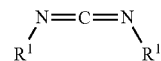

and a byproduct derived from:

wherein $R^1$, $R^2$ and $R^3$ are as described above with respect to a compound of Formula (I). The carbodiimide is then believed to readily react with another present persistent carbene to from the persistent carbene-carbodiimide adduct. A non-limiting example of the mechanism is shown in FIG. 2.

It has been discovered that the persistent carbene-adducts described herein have different chemical properties than previously described persistent carbene-adducts. In some embodiments, for certain compounds of Formula (I), the different chemical properties may be attributed to the method of formation or the properties of $R^1$ attached to the carbodiimide. Without wishing to be bound by theory, it is believed that persistent carbene-adducts formed by heating and/or having at least one $R^1$ (e.g., one $R^1$, two $R^1$) attached to the carbodiimide that is sterically bulky (e.g., optionally substituted aryl, optionally substituted unsaturated moiety) may have different bond geometries compared to persistent carbene-adducts formed by another method and/or lacking one or more sterically bulky group attached to the carbodiimide.

In some embodiments, the differences in bond geometries (e.g., bond angles) result in the persistent carbene-adducts having different chemical properties, such as chemical reactivity and stability in certain environments (e.g., in solutions comprising water). For example, a precursor may be heated to form a compound of Formula (I) wherein the two $R^1$ attached to the carbodiimide are the same or different and are optionally substituted aryl. This compound of Formula (I) formed by heating may have a —N—C═N— bond angle that is at least 10° greater than a compound of Formula (I) formed via a different method, such as direct addition of a persistent carbene to a carbodiimide that is not produced in situ and/or derived from a persistent carbene, and/or lacking one or more sterically bulky group attached to the carbodiimide. For instance, the —N—C═N— bond angle of a compound of Formula (I) wherein the two $R^1$ attached to the carbodiimide are the same or different and optionally substituted aryl formed by heating may be about 140°; whereas the a compound of Formula (I) formed by direct addition and/or lacking one or more sterically bulky group attached to the carbodiimide may have a —N—C═N— bond angle of 130°.

The difference in —N—C═N— bond angle may lead to significant difference in chemical reactivity and spectroscopic properties. For instance, persistent carbene-carbodiimide adducts formed via heating may have a zwitterionic nature, have mild Lewis basicity, and be stable in ambient conditions and environments containing water. As an example, a compound of Formula (I) wherein $R^1$ are the same or different and optionally substituted aryl formed via heating may be relatively stable in environments comprising water, such as solvent mixtures containing water. Whereas, a compound of Formula (I) formed via a different method and/or lacking one or more sterically bulky group attached to the carbodiimide may be more basic and deprotonate the water, resulting in the decomposition of the compound of Formula (I).

It should be understood that the method step may be performed without any additional reactants besides the precursor compounds. That is, compounds of Formula (I) may be formed by simply heating the precursor compounds, described herein, such that the method step consists of or consists essentially of heating a precursor compound to a suitable temperature for a suitable time. For example, a method for forming a compound of Formula (I) (or a tautomer thereof) may consist of or consist essentially of the step of heating a precursor compound, described herein, optionally in a solvent, to a temperature of about 80° C. or greater, wherein the percent conversion to the compound is greater than or equal to 50%.

As described herein, the percent conversion of the precursor compound to a compound of Formula (I). As used herein "percent conversion" refers to the percent yield of the chemical reaction. The percent yield may be represented by the following formula: percent yield=(actual yield/theoretical yield)×100. In some embodiments, the percent conversion may be greater than or equal to about 50%, greater than or equal to about 60%, greater than or equal to about 70%, greater than or equal to about 75%, greater than or equal to about 80%, greater than or equal to about 85%, greater than or equal to about 90%, greater than or equal to about 95%, greater than or equal to about 97%, or greater than or equal to about 98%. Those of ordinary skill in the art will be aware of methods for determining the percent conversion of a compound, for example, via $^1H$ NMR.

As noted above, a persistent carbene-carbodiimide adduct may be formed by heating the a precursor compound to relatively high temperatures. In some embodiments, the heating step may comprising heating the precursor compound to a temperature greater than or equal to about 80° C., greater than or equal to about 90° C., greater than or equal to about 100° C., greater than or equal to about 110° C., greater than or equal to about 120° C., greater than or equal to about 130° C., or greater than or equal to about 140° C. In certain embodiments, the heating step may comprising heating the precursor compound to a temperature between about 80° C. to about 150° C., between about 90° C. to about 150° C., between about 100° C. to about 150° C., between about 80° C. to about 140° C., between about 90° C. to about 140° C., between about 100° C. to about 140° C., between about 80° C. to about 130° C., between about 90° C. to about 130° C., or between about 100° C. to about 130° C.

In some embodiments, the heating step may be carried out for greater than or equal to about 30 minutes, greater than or equal to about 45 minutes, greater than or equal to about 60 minutes, about 2 hours, greater than or equal to about 4 hours, greater than or equal to about 6 hours, greater than or equal to about 8 hours, greater than or equal to about 12 hours, greater than or equal to about 18 hours, greater than or equal to about 24 hours, greater than or equal to about 48 hours, greater than or equal about 72 hours, or greater. In some cases, the period of time is between about 1 hour and about 48 hours, between about 2 hours and about 48 hours, between about 4 hours and about 48 hours, between about 6 hours and about 48 hours, or between about 1 hour and about 24 hours. In certain embodiments, precursor compounds comprising a thermolabile protecting group may be heated for a longer period of time. For instance, in some embodiments, the heating step for a precursor compound with a thermolabile protecting group may be carried out for between about 1 hour and about 504 hours, between about 12 hours and about 504 hours, between about 24 hours and about 504 hours, between about 48 hours and about 504 hours, or between about 72 hours and about 504 hours.

In some embodiments, the heating step may be conducted with the precursor compound dissolved or dispersed in one or more solvents. In some embodiments, the solvent is chosen such that the precursor compound and persistent carbene adduct are at least partially soluble. Non-limiting examples of suitable solvents include tetrahydrofuran, acetonitrile, dimethylformamide, dichloromethane, benzene, 1,2-dichlorobenzene toluene, hexanes, xylene, diethyl ether, dioxane, dimethylsulfoxide, ethyl acetate, pyridine, triethylamine, or combinations thereof (e.g., 10:1 chloroform:methanol). In some embodiments, the concentration of the precursor compound in the one or more solvents may be between about 0.001 M and about 4 M, between about 0.001 M and about 3 M, between about 0.001 M and about 2 M, between about 0.001 M and about 1 M, between about 0.005 M and about 1 M, between about 0.01 M and about 1 M, between about 0.05 M and about 1 M, or between about 0.1 M and about 1 M.

In some embodiments, a compound of Formula (I), as described above, may be relatively stable under certain conditions. For instance, the compound of Formula (I) may be relatively stable at ambient conditions (i.e., temperature of 20° C., a pressure of 1 atm, and a relative humidity of about 50%) and/or aqueous containing solvents. For instance in some embodiments, compounds of Formula (I) may be stable at ambient conditions and/or solvents containing 10 wt. % of water for greater than or equal to about 12 hours, greater than or equal to about 18 hours, greater than or equal to about 24 hours, greater than or equal to about 36 hours, greater than or equal to about 48 hours, greater than or equal to about 72 hours, greater than or equal to about 1 week, greater than or equal to about 6 week, greater than or equal to about 12 week, greater than or equal to about 24 week, greater than or equal to about 1 year. Stability of the compound may be determined by monitoring the change in the $^1$H NMR spectra over time. A compound of Formula (I) is considered stable if no peak that is indicative of a compound of Formula (I) has a change in peak height of more than 10%.

As mentioned above, compounds of Formula (I) may be used for a variety of applications including organometallic chemistry, catalysis, surface functionalization, and sensing, amongst others. In some embodiments, compounds of Formula (I) may be used as amidinate ligands for Lewis acidic metal cations. Non-limiting examples of suitable Lewis acidic metal cations include Li, Be, Na, Mg, Al, K, Ca, Sc, Ti, V, Cr, Mn, Fe, Co, Ni, Cu, Zn, Ga, Rb, Sr, Y, Zr, Nb, Mo, Tc, Ru, Rh, Pd, Ag, Cd, In, Sn, Sb, Cs, Ba, La (and other lanthanides), Hf, Ta, W, Re, Os, Ir, Pt, Au, Hg, Tl, Pb, Bi, Ac, Th, Pa, U, Np, and Pu (and other actinides). In some embodiments, the metal cations may undergo detectable spectroscopic changes (e.g., change in absorption wavelength) after binding to a compound of Formula (I). In some such cases, compounds of Formula may be used as a sensor for free Lewis acidic metal cations in solution by detecting a change in a spectroscopic property of the solution.

For convenience, certain terms employed in the specification, examples, and appended claims are listed here.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999, the entire contents of which are incorporated herein by reference.

As used herein, the term "persistent carbene" is given its ordinary meaning in the art and refers to a stable carbene (e.g., demonstrating certain stability despite being a reactive intermediate. In some embodiments, the persistent carbene is an N-heterocyclic carbene ("NHC"). Non-limiting examples of persistent carbenes include diaminocarbenes (e.g., imidazol-2-ylidenes, benzimidazol-2-ylidenes, imidazolidin-2-ylidenes, triazol-5-ylidenes, diaminocarbene incorporated into a n-membered ring of size, where n is not five), heteroaminocarbenes (e.g., thiazol-2-ylidenes and oxazol-2-ylidenes), and mesoionic carbenes (e.g., imidazol-4-ylidenes, 1,2,3-triazol-4(or -5)-ylidenes, pyrazol-3(or -4)-ylidenes, isoxazol-4-ylidenes, and thiazol-5-ylidenes).

It should be understood that the persistent carbenes and persistent carbene adducts described herein may also be provided as homologs, analogs, derivatives, enantiomers, diastereomers, tautomers, and cis- and trans-isomers of compounds described herein. It will be understood that the skilled artisan will be able to manipulate the conditions in a manner to prepare such homologs, analogs, derivatives, enantiomers, diastereomers, tautomers, and cis- and trans-isomers, and functionally equivalent compositions.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

As used herein, the term "tautomer" refers to particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched, and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched, or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6, or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched, or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_R$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls, and/or heterocyclyls. The aryl group may be optionally substituted, as described herein. Substituents include, but are not limited to, any of the previously mentioned substituents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substituents, i.e., the substitutes recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl) heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_R$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycyclic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "halo" and "halogen" as used herein refer to an atom selected from the group consisting of fluorine, chlorine, bromine, and iodine.

The term "amino," as used herein, refers to a primary ($-NH_2$), secondary ($-NHR_x$), tertiary ($-NR_xR_y$), or quaternary ($-N^+R_xR_yR_z$) amine, where $R_x$, $R_y$, and $R_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy, and n-hexoxy. Examples of thioalkyl include, but are not limited to, methylthio, ethylthio, propylthio, isopropylthio, n-butylthio, and the like.

The term "acyl" refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes ($-CHO$), carboxylic acids ($-CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "thiol" or "thio" refers to the group $-SH$. The term "substituted thiol" or "substituted thio," by extension, refers to a thiol group wherein the sulfur atom directly attached to the parent molecule is substituted with a group other than hydrogen, and includes groups selected from $-SR^{aa}$, $-S=SR^{cc}$, $-SC(=S)SR^{aa}$, $-SC(=O)SR^{aa}$, $-SC(=O)OR^{aa}$, and $-SC(=O)R^{aa}$, wherein $R^{aa}$ and $R^{cc}$ are as defined herein.

each instance of $R^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently optionally substituted;

each instance of $R^{bb}$ is, independently, selected from hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently optionally substituted;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently optionally substituted.

As used herein, the term "phosphine" is given its ordinary meaning in the art and refers to a group comprising at least one phosphorus atom. The phosphorus atom may bear one, two, or three aliphatic or aromatic groups, optionally substituted and optionally comprising at least one heteroatom.

As used herein the term "sulfide" is given its ordinary meaning in the art and refers to a group comprising —S—$R^{aa}$, wherein $R^{aa}$ is as described herein.

As used herein the term "azide" is given its ordinary meaning in the art and refers to a group comprising —$N_3$.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether proceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful for the formation of an imaging agent or an imaging agent precursor. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

EXAMPLES

Abstract:

For over two decades, the chemistry of N-heterocyclic carbenes has been the subject of intensive research interest. This example the discovery of a previously unknown, yet surprisingly general, reaction manifold is described for one of the most widely studied and important classes of NHCs: 1,3-bis(aryl)imidazolidin-2-ylidenes, of which the commercially available "SIMes" is perhaps the most well-known member. It was found that upon mild heating (temperatures as low as 80° C.) these species converted cleanly and quantitatively to unprecedented crystalline NHC-bis(aryl) carbodiimide adducts. Mechanistic analysis revealed that this process proceeded via a first-order [3+2]-cycloelimination reaction of the imidazolidin-2-ylidene to generate ethylene gas and bis(aryl) carbodiimide (CDI), the latter of which was immediately trapped by a second equivalent of NHC. The CDI fragment of these adducts displayed a remarkably large N—C—N angle (~140°), which stemmed from the large steric bulk of both the NHC and CDI components within the adduct. Despite this spring-loaded bonding geometry, these zwitterionic compounds were thermally and air-stable both in the solid state and in solution. Furthermore, these adducts possessed a Lewis-basic amidinate functionality, which can be used as a novel ligand scaffold for Lewis-acidic metals (e.g., $Sc(OTf)_3$, $Zn(OTf)_2$, and $Ni(OTf)_2$). Given the widespread application of SIMes and related NHCs in the fields of catalysis, organometallic chemistry, and surface chemistry during the course of the past two decades, the absence of precedent for this reactivity was surprising. With that in mind, we believe that this findings, which constitute the first identification and mechanistic elucidation of a thermally activated NHC [3+2]-cycloelimination, and the development of a new metal ligand class based on NHC-CDI adducts, are of broad fundamental importance.

Discussion:

Since Arduengo's isolation of the first crystalline N-heterocyclic carbene (NHC) in 1991, the unique properties of these species have led to their pervasive use in fields including main group and organometallic chemistry, catalysis, medicinal chemistry, and materials science. Amongst the various classes of NHCs, the 1,3-bis(aryl) imidazolidin-2-ylidenes, are perhaps the most famous. As a testament to the general importance of this class of NHCs, SIMes and 1,3-bis(2,6-di-i-propylphenyl)imidazolidin-2-ylidene (SiPr) are two of only a handful of free carbenes that are commercially available from large chemical suppliers.

In an efforts to further extend the utility of NHCs for materials applications, Si—H insertion reactions between 1a showing in FIG. 1A tris(trimethylsilyl)silane were investigated. The insertion did not occur under normal reaction conditions. In an attempt to drive the reaction, the reaction mixture was heated to temperatures not typically utilized. When this reaction mixture was heated to 100° C. in an effort to facilitate Si—H insertion, a yellow precipitate was formed. $^1$H nuclear magnetic resonance (NMR) spectroscopy, high-resolution mass spectrometry, and X-ray crystallographic analysis revealed this product to be the unexpected NHC-carbodiimide (CDI) adduct 2a shown in FIG. 1B. Further studies revealed that tris(trimethylsilyl)silane was not necessary for the formation of 2a; simply heating a solution of 1a in toluene induced its quantitative conversion to 2a. Furthermore, 1a converted cleanly to 2a in the more polar 1,2-dichlorobenzene-d$^4$ where 2a remained fully soluble throughout most of the course of the reaction. Lastly, the reaction was not limited to 1a; analogous bis(chloro) (1b) and bis(fluoro) (1c) derivatives, the parent NHC SIMes, and the bench stable NHC—$CO_2$ adduct 1a-$CO_2$, which generates NHC 1a upon thermal elimination of $CO_2$, all cleanly provided the NHC-CDI adducts—2b, 2c, SICDI (i.e., SIMes-CDI) shown in FIG. 1C, and 2a, respectively—under similar conditions. In the case of the NHC—CO2 adduct, the decarboxylation increases the reaction time (vide infra). In this case, complete formation of 2a required heating at 115° C. for 1 week.

FIG. 1 shows (A) the transformation of NHCs and NHC—$CO_2$ adducts to corresponding NHC-CDI adducts, (B) the crystal structure of 2a (disorder is shown in the location of the left N-substituent in the crystal structure), R(F)=0.0289, $R_w(F^2)$=0.0711, and (C) the crystal structure of SICDI, R(F)=0.0460, $R_w(F^2)$=0.1367.

Structure of NHC-CDIs:

Single crystal X-ray structures of NHC-CDI adducts 2a and SICDI are shown in FIGS. 1B and 1C. Crystals in all cases but 2a were grown during the course of the cycloelimination reaction in toluene-d8 at 100±5° C. in a J-Young NMR tube. Crystals of 2a were grown by vapor diffusion of toluene into a THF-d8 solution of 2a. The four compounds share structural similarities: the NHC-CDI C—C bond length was 1.50-1.51 Å, the NHC and CDI C—N bond lengths were 1.32-1.33 Å, the CDI N—C=N bond angles were 139.61-140.02°, and the NHC N—C=N bond angles were 110.96-111.26°. These values agree within 2% with the values computed using DFT with B3LYP functional, a 6-31G** basis set, and the symmetry constraint. Interestingly, the dihedral angle between the NHC and CDI (Newman projections provided for 2a and SICDI in FIGS. 1B and 1C) exhibited more variation: 63.32° for 2b, 65.51° for 2a, 67.02° for 2c, and 85.18° for SICDI. The large difference between halogenated adducts 2a-c and SICDI suggested the presence of favorable interactions between the electron deficient aryl substituent of the former compounds with the electron rich CDI component. The dihedral angles computed by DFT ranged from 69.11° to 74.00° for the different adducts, which suggested the presence of a rotational freedom of +/−3° of the structures about the NHC—CDI bond. Notably, the CDI aryl groups were also rotated about the $C_{ipso}$—N bond by 28-39° relative to the normal to the C—N—$C_{ipso}$ plane. This rotation staggers the proximal "ortho" methyl H atoms of the two CDI aryl substituents, presumably to relieve van der Waals strain. The distance between these H atoms was greater than it would have been in the "pseudo-eclipsed" conformation, but it was still equal to or slightly less than the sum of their van der Waals radii (2.18 Å). Additionally, in all cases, the distances between the N atoms of the CDI and the proximal H atoms of the NHC ortho-methyl groups were slightly greater (~0.1 Å) than the sum of their van der Waals radii (1.09 Å+1.55 Å=2.64 Å) and similar to distances observed in other examples of weak C—H—N hydrogen bonds. These observations suggested that weak C—H—N hydrogen bonds could play a role in the solid-state geometry of the NHC-CDI adducts.

FIG. 2 shows the proposed mechanism for the transformation of 1a into 2a and ethylene. Conversion with time in o-dichlorobenzene-d$^4$ at 100±5° C. (in a sand bath) was monitored via $^1$H NMR.

The NHC-CDI adducts described herein were stable in the presence of moisture for at least 3 d, as confirmed by $^1$H NMR in MeCN-d$^3$. Furthermore, treatment of SICDI with benzoic acid in anhydrous $CD_2Cl_2$ leads to rapid protonation of SICDI without decomposition. Interestingly, over the course of several days $^1$H NMR spectroscopy suggests that over the course of several days benzoate further reacts with this protonated species to generate a new, stable adduct. Lastly, the NHC-CDI adducts exhibit previously unreported absorbance in the visible region and violet-indigo fluorescence (389-422 nm); these optical properties arose from conjugation across the CDI component, which was apparent in the DFT-computed HOMO (vide infra).

Figure 3:
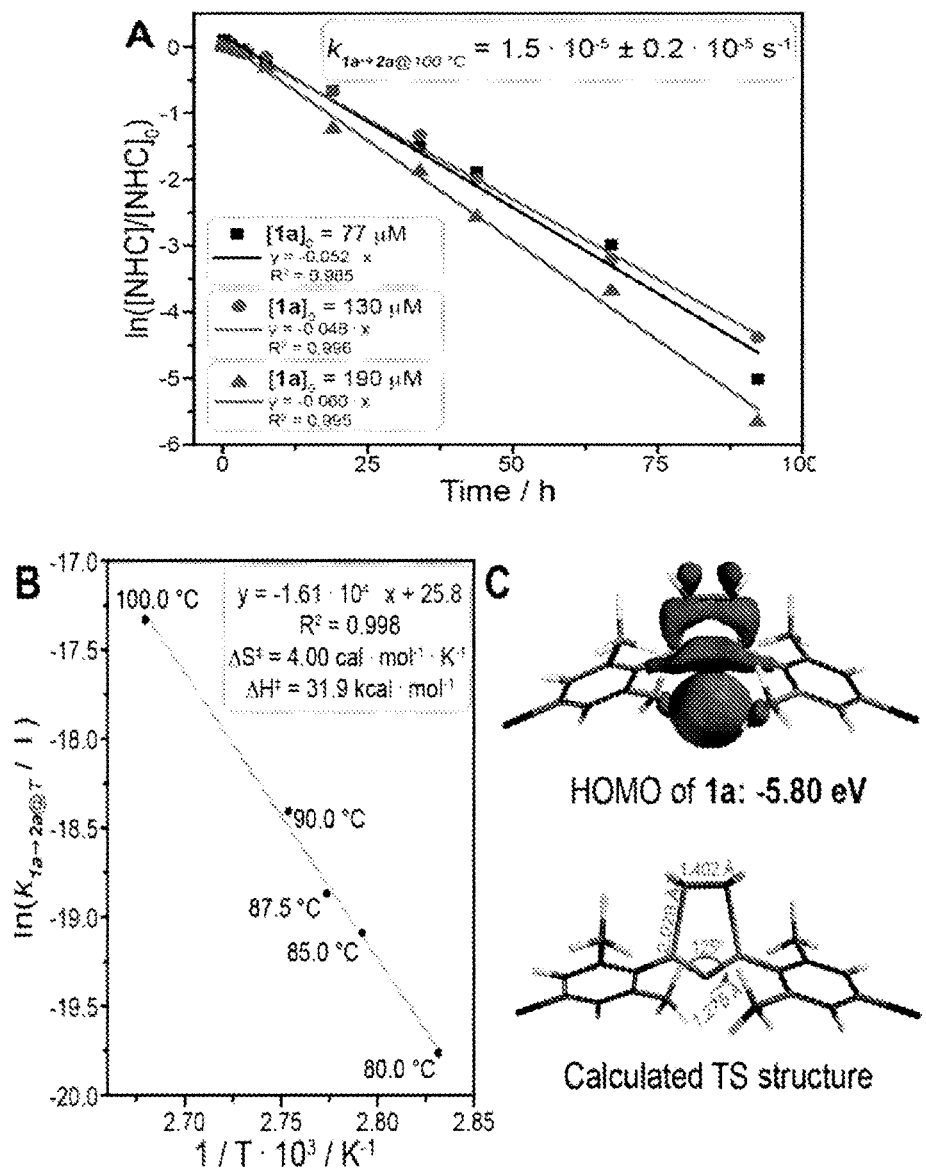
FIG. 3A shows a graph of $\ln([NHC]_{norm})$ vs time for the conversion of the N-heterocyclic carbene into the N-heterocyclic-carbodiimide, according to certain embodiments.
FIG. 3B shows the Eyring plot for the conversion of the N-heterocyclic carbene into the N-heterocyclic-carbodiimide, according to certain embodiments.
FIG. 3C shows a schematic of the HOMO orbital of the N-heterocyclic carbene and its cycloelimination TS≠structure calculated using DFT with B3LYP functional, and 6-31G** basis set, according to certain embodiments.

FIG. 3(A) shows the reaction order determination through monitoring consumption of 1a with time for different [NHC]$_o$ in toluene-d$^8$ at 100+/−5° C. in a sand bath. [NHC] was normalized to the residual solvent peak at 2.08 ppm. The linear plot of ln([NHC]$_{norm}$) vs time indicates a first-order rate dependence. The apparent insensitivity of rate to [NHC]$_o$ confirms the first-order dependence. FIG. 3(B) shows the Eyring plot for the NHC conversion to the NHC-CDI in toluene-d$^8$ in a sealed J-Young NMR tube in an oil bath with a temperature variation of +/−2° C. FIG. 3C shows the HOMO orbital of 1a and its cycloelimination TS$^‡$ structure calculated using DFT with B3LYP functional, and 6-31G** basis set.

Mechanistic Investigations:

The mechanism for this NHC-CDI formation reaction was investigated. It was hypothesized that our NHC-CDI adducts could form via a two-step mechanism that consisted of a [3+2]-cycloelimination of 1,3-bis(aryl) imidazolidin-2-ylidene NHC to generate a 1,3-bis(aryl) CDI, followed by trapping of this CDI with a second NHC. Though such a transformation has not been reported, mechanistic analogues for both of steps are known.

Various experimental investigations supported this mechanistic proposal. First, direct $^1$H NMR analysis of the reaction, as shown in FIG. 2, revealed the formation of ethylene and no other byproducts. Notably, free CDI was not observed, which suggests that the [3+2]-cycloelimination is rate-limiting. The kinetic analysis shown in FIG. 3A supports this notion. The rate constants for the cycloelimination process obtained for a series of reactions run at various [1a]$_o$ values were virtually identical (7.4±0.7 10$^{-6}$ s$^{-1}$ at 100±5° C.), which suggested an overall reaction order of one. The heating for these three experiments was carried out in a sand bath. While these experiments were self-consistent, the temperature variation (±5° C.) throughout the sand bath accounts for the ~25% disparity with the values obtained for the Eyring plot, which were all measured in silicone oil bath, which had a much smaller temperature variation (±2° C.). Note that the half-life of this reaction ($t_{1/2}$=26 h at 100±5° C.) reflects the rate of the [3+2]-cycloelimination process. The Eyring analysis shown in FIG. 3B provided activation parameters ΔS≠ and ΔH≠ of +2.62 cal/mol.K and +31.9 kcal/mol, respectively. These values were consistent with the proposed rate-limiting cycloelimination mechanism wherein 1 transitions to ethylene and CDI via concerted breakage of two C—C σ bonds and formation of one C=C π bond and two N=C bonds in the transition state. The magnitude and sign of ΔS≠ were consistent with other examples of cycloelimination reactions.

Additional evidence for the proposed [3+2]-cycloelimination came from density functional theory (DFT) geometry optimization performed on NHCs 1a-c and SIMes. Examination of the ground state HOMO, LUMO, and LUMO+1 (approximately degenerate with LUMO in all cases) orbitals (calculated in a vacuum) revealed two key features: (1) the largest orbital coefficient of the HOMO was on the carbene carbon, and (2) in both the HOMO and LUMO+1 there were orbitals present on the NHC $CH_2$—$CH_2$ backbone with correct geometry and relative symmetry to form the π bond of the eliminated ethylene. Following the Woodward-Hoffmann rules, it was expected that the proposed [3+2]-cycloelimination involving six electrons would be thermally allowed. Moreover, the proposed reaction path—"linear" departure of ethylene, in analogy with linear departure of CO from cyclopentenone—would proceed along a least-motion path while maintaining the greatest amount of bonding character in the germane orbitals. Hence, the proposed concerted reaction mechanism was justified from the standpoint of orbital considerations. Finally, the transition state geometry for cycloelimination was modeled using DFT after an initial optimization via a semi-empirical PM3 model as shown in FIG. 3C. Beginning with the initial, DFT-optimized ground state (GS) geometry, the bond lengths between the NHC nitrogen atoms and the NHC backbone carbon atoms were constrained to be progressively larger values (Δ(bond length)=0.1 A), until ethylene and CDI formed. At each stage, the GS geometry of the structure was optimized using the semi-empirical PM3 model. Once an energy maximum was reached, the corresponding geometry was used as a guess for the transition state (TS) geometry optimization using DFT with a B3LYP functional and 6-31G** basis set. The ΔH≠ evaluated by subtracting the energy of the starting NHC from the TS energy. In the transition state, the NHC N—C=N angle had increased from 105.58° in the ground state of 1a to 125.00°, and the N—$C_{backbone}$ bond lengths had increased from 1.490 Å to 2.029 Å. The computed ΔH≠ was 29.8 kcal/mol, which was remarkably close to the observed value obtained via Eyring analysis and, consistent with the small errors typical for the DFT methods in transition state energy calculations of unimolecular reactions (mean unsigned error=2.49 kcal/mol).

Lastly, it was found that upon heating of a mixture of SIMES-CDI and 2a in toluene at 100° C. for seven hours, the two adducts underwent exchange of NHC and CDI partners, as confirmed by $^1$H NMR and LCMS. This observation of cross-over implies the presence of an equilibrium between the NHC and CDI and their adduct. DFT calculations estimated the ΔH° for the dissociation of 2a into the NHC and CDI fragments to be 13.0 kcal/mol, implying an overall ΔH≠ of 13.0+29.8 kcal/mol=42.8 kcal/mol for the conversion of 2a to two equivalents of the corresponding CDI and one equivalent of ethylene.

Applications of NHC-CDIs:

Given the ease of NHC-CDI adduct formation directly from commercially available SIMes, its substituted analogs, and stable NHC—$CO_2$ adducts, their zwitterionic nature, mild Lewis basicity, and stability under ambient conditions, we envision a range of possible applications for these novel structures was envisioned. For example, it was hypothesized that the Lewis basic CDI component of these adducts could serve as an amidinate ligand for Lewis acidic metal cations. In this case, metal binding would disrupt the conjugation of the CDI fragment, and potentially offer a means for absorption-based sensing of metal cations in solution. Furthermore, the development of a new amidinate ligand scaffold could find applications in transitional metal catalysis. In all reported cases of amidinate-metal complexes the amidinate geometry has been starkly different than would be expected for the new NHC-CDI adducts reported here: in contrast to the usual bidentate coordination of the amidinate moiety, these adducts would present a small binding pocket for $η^1$-type coordination to the metal species.

Figure 4:
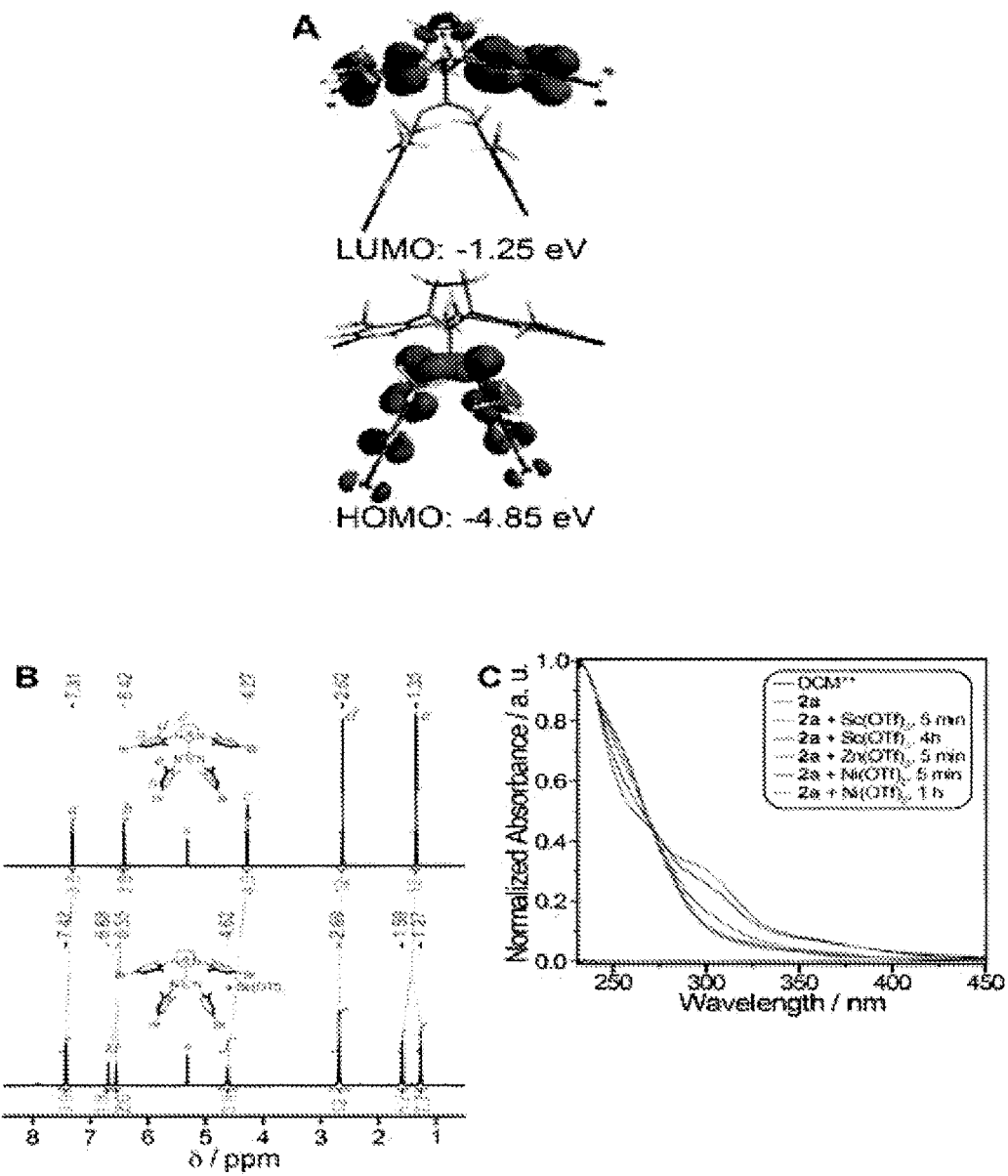
FIG. 4A shows DFT-calculated frontier molecular orbitals of the N-heterocyclic-carbodiimide, according to certain embodiments.
FIG. 4B shows $^1H$ NMR spectrum of the N-heterocyclic-carbodiimide and of the N-heterocyclic-carbodiimide plus $Sc(OTf)_3$, according to certain embodiments.
FIG. 4C shows UV-vis spectroscopy of the N-heterocyclic-carbodiimide before and after exposure to a range of metal triflates, according to certain embodiments.

FIG. 4 shows (A) the DFT-calculated frontier molecular orbitals of adduct 2a, (B) the $^1$H NMR spectra (400 MHz, RT) of 2a and 2a+Sc(OTf)$_3$ in DCM-d$^2$, and (C) the UV-vis spectroscopy of 2a before and after exposure to a range of metal triflates. *DCM-d$^2$ residual solvent peak; **absolute (not normalized) absorbance is plotted.

DFT calculations revealed that the NHC-CDI HOMO was delocalized over the CDI fragment (amidinate), while the LUMO was delocalized over the NHC fragment as shown in FIG. 4A. The largest orbital coefficients in the HOMO were at the CDI nitrogen atoms; this observation suggested that these nitrogen atoms would be the sites of coordination for Lewis acidic metal species. Such 1:1 $η^1$-type coordination would desymmetrize the CDI fragment in the complex, and localize the previously delocalized electron density. Both of these features have been confirmed with NHC-CDI adduct 2a via $^1$H NMR and UV-vis spectroscopy. Exposure of the adduct to a ~6-fold excess of Sc(OTf)$_3$ in DCM-d$^2$ for less than 5 min led to loss of yellow color and resulted in nearly quantitative splitting of the CDI $^1$H NMR resonances b and e as shown in FIG. 4B; moreover, all but one $^1$H resonance exhibited a downfield shift. These transformations were indicative of NHC-CDI complexation with the Lewis-acidic Sc$^{III}$ with the concomitant structural desymmetrization expected in the formation of an $η^1$-coordination complex. The latter was completely stable under inert atmosphere at room temperature for at least 5 hours, as indicated by $^1$H NMR. FTICR-MS analysis (positive ion mode) of the resulting solution exhibited solely the protonated form of 2a, which indicated that the N—Sc coordination was weak, and confirmed that the integrity of the NHC-CDI framework was preserved, as expected for the proposed coordination.

The UV-vis spectrum of 2a in DCM, shown in FIG. 4C, showed a series of transitions above 250 nm, with non-zero absorbance that extends to >450 nm. In particular, a clear peak at 294 nm ($λ_{max}$≈294 nm, ϵ=7750 M$^-$cm$^{-1}$) was observed for all of the NHC-CDI adducts. Complexation of 2a (1.56 mM) with Sc(OTf)$_3$ led to loss of this peak as well as a decrease in absorbance at all longer wavelengths. These solutions were diluted ~61-fold for UV-vis spectroscopy.

Hence, this UV-vis resonance at 294 nm was attributed to an excitation of the electrons residing in the HOMO of 2a. The resonance energy exceeded the calculated HOMO-LUMO energy gap by 0.62 eV, and therefore likely corresponds to a HOMO-(LUMO+1) transition or a transition to a higher-lying vibrational state of the LUMO. Similar UV-vis spectral changes were observed upon treatment of 2a with excess $Zn(OTf)_2$; a similar transformation with $Ni(OTf)_2$ proceeded as well, albeit more slowly, requiring ~1 h to eliminate the germane absorbance resonance of 2a. In all cases, complexation was accompanied by disappearance (partial in the case of $Ni(OTf)_2$) of the yellow color of the NHC-CDI solution. The described complexation behavior is more general both with regard to the NHC-CDI and the solvent: thus, treatment of SIMES-CDI with excess Zn(OTf)2 and Ni(OTf)2 in MeCN-d3 led to the quantitative formation of 1:1 ligand-metal complexes, as indicated by 1H NMR. These results rendered NHC-CDI adducts promising targets for metal ion sensors and as photoactive ligands in transition metal photocatalysis.

To summarize, a novel reaction manifold for NHCs of the SIMes family has been discovered: namely [3+2]-cycloelimination into ethylene and a carbodiimide; the latter was trapped by another equivalent of the NHC to generate novel NHC-CDI adducts. This reaction did not proceed for IMes at 100° C.—the partial aromatic character of the imidazolylidene ring in IMes likely rendered it more stable. These novel cycloeliminations are examples of a potentially broad class of pericyclic reactions. Furthermore, these reactions constitute a new route toward NHC-CDI adducts; moreover, veiled NHC (e.g., $CO_2$ adducts, vide supra) which liberate the NHC when heated or photoirradiated may also be suitable starting materials. Lastly, the photoactivity and mild Lewis-basicity of the NHC-CDI adducts make them a promising new ligand platform for metal-mediated photocatalysis and for metal ion sensing and numerous other applications.

Materials and Analytical Methods:

1,3-Bis(2,4,6-trimethylphenyl)-4,5-dihydroimidazol-2-ylidene (SIMes), 1,3-bis(2,4,6-trimethylphenyl)imidazol-2-ylidene (IMes), 1M solution of potassium hexamethyldisilazide (KHMDS) in tetrahydrofuran (THF), and non-deuterated solvents were purchased from Sigma-Aldrich®. Scandium(III) trifluoromethylsulfonate ($Sc(OTf)_3$) was purchased from Alfa Aesar® (distributed by VWR®). Zinc(II) trifluoromethanesulfonate ($Zn(OTf)_2$) and nickel(II) trifluoromethanesulfonate ($Ni(OTf)_2$) were purchased from Strem Chemicals, Inc. All deuterated solvents were purchased from Cambridge Isotope Laboratories, Inc. All other reagents and solvents were purchased from VWR® or Sigma-Aldrich®. All purchased reagents and solvents were used as supplied unless otherwise noted. Solvents not in Sure/Seal™ containers were degassed (unless supplied in ampules under inert atmosphere) via three freeze-pump-thaw cycles and dried over 3 Å molecular sieves (from Mallinckrodt Baker) prior to use in air-sensitive experiments (i.e., ones involving the use of N-heterocyclic carbenes). All air-sensitive reactions were executed in a nitrogen-atmosphere glove box or using standard Schlenk techniques using glassware dried for at least 6 h at 120° C.

Liquid chromatography-mass spectrometry (LC/MS) were performed on an Agilent 1260 LC system equipped with an Advanced Materials Technology HALO® C18 high performance column. Solvent gradients consisted of mixtures of nano-pure water with 0.1% acetic acid (AcOH) and HPLC-grade acetonitrile. Mass spectra were obtained using an Agilent 6130 single quadrupole mass spectrometer.

$^1H$ nuclear magnetic resonance ($^1H$ NMR), $^{13}C$ nuclear magnetic resonance ($^{13}C$ NMR), and $^{19}F$ nuclear magnetic resonance ($^{19}F$ NMR) spectra were recorded on two Bruker AVANCE-400 NMR spectrometers. Chemical shifts are expressed in parts per million (ppm), and splitting patterns are designated as s (singlet), d (doublet), t (triplet). Coupling constants J are reported in Hertz (Hz). MestReNova LITE v5.2.5-4119 software (Mestrelab Research S.L.) was used to analyze the NMR spectra. $^1H$ and $^{13}C$ NMR spectra were referenced to solvent peaks as reported in literature.(68) The residual solvent resonances of ODCB-$d^4$ were referenced to 7.19 and 6.93 ppm. $^{19}F$ NMR spectra were referenced using an external reference of neat $CFCl_3$ ($\delta$=0.00).

High-resolution mass spectrometry (HRMS) was obtained using a Bruker Daltonics APEXIV 4.7 Tesla Fourier Transform Ion Cyclotron Resonance Mass Spectrometer (FT-ICR-MS).

Ultraviolet-visible (UV-vis) spectroscopy was carried out using a Varian Cary® 50 Scan UV-Vis Spectrophotometer. The spectra were collected in dual beam mode at 600 nm/min from 800 to 200 nm, using 100% T baseline correction based on a sample of neat solvent (HPLC grade) in a quartz cuvette used for the subsequent measurements. The spectra were analyzed using the Cary WinUV software.

Fourier-transform infra-red attenuated total reflectance (FTIR-ATR) spectroscopy was carried out using a Thermo Scientific Nicolet 6700 FT-IR equipped with a germanium ATR crystal. A background spectrum was collected prior to spectroscopy of the samples, and 64 scans were collected and averaged for both background and samples. OMNIC™ software was used to analyze the IR data: no corrections were applied to the spectra shown below. Resonance energies are expressed in wavenumbers ($cm^{-1}$), and resonances are designated as s (strong), m (medium), w (weak), or br (broad).

Fluorimetry was carried out using Fluorolog®-3 spectrofluorometer from Jobin Yvon Horiba using the DataMax for Windows™ driving software. The following parameters were used during the fluorimetry: (1) integration time=0.25 s; (2) increment=1 nm; (3) excitation wavelength: variable; (4) Detector HV S=950 V and R=0 V; bandpass slits: excitation1=3.000 nm; emission1=5.000 nm. The data was analyzed using OMNIC™ software and plotted in OriginPro 8.5.

Melting point analysis was carried out using Mel-Temp® II from Laboratory Device, Inc., USA.

Computational Details:

All computations were done using Spartan 10 (version 1.1.0). Geometry optimizations were performed using density functional theory (DFT) with the B3LYP exchange-correlation functional and 6-31G basis set. The symmetry constraint was implemented in each case. For transition state optimizations, the following approach was implemented. Following the initial, DFT-optimized ground state (GS) geometry, the bond lengths between the NHC nitrogen atoms and the NHC backbone carbon atoms were constrained to be progressively larger values ($\Delta$(bond length)= 0.1 Å), until ethylene and CDI formed: progressively moving the two fragments apart approximates the proposed reaction coordinate. At each step, the GS geometry of the structure was optimized using the semi-empirical PM3 model to approximate points along the reaction coordinate-energy profile for the cycloelimination process. Once an energy maximum was reached, the corresponding geometry was used as a guess for the transition state (TS) geometry optimization using first PM3 and then DFT with a B3LYP functional and 6-31G basis set. The vibrational frequencies were then calculated using DFT with a B3LYP functional and 6-31G** basis set, revealing a single imaginary frequency of 483.07i cm$^{-1}$. The $\Delta H^{\#}$ was evaluated by subtracting the total energy (as defined in Spartan) of the starting NHC from the TS energy. Orbital energies in a solvent were calculated using the SM8 model for the selected solvent.

Synthesis and Characterization of N-Heterocyclic Carbenes:

1,3-bis(4-bromo-2,6-dimethylphenyl)-4,5-dihydroimidazol-2-ylidene 1a

To 4.73 g (10.0 mmol) of imidazolium salt 1a HCl in a 40-mL scintillation vial in the glove box was added 10 mL anhydrous THF followed by 10. mL of 1.0 M KHMDS solution in THF (10. mmol, 1.0 equiv). The vial was closed and the mixture was agitated for 5-10 min until all of the 1a HCl had gone into solution, with concomitant formation of suspended fine KCl particulates. The reaction mixture was filtered through a 0.45 μm PTFE syringe filter (NOTE: these syringe filters are easily clogged; four filters had to be used to accomplish complete filtration). The solution was concentrated to dryness on the Schlenk line. The resulting crystalline solid was crushed to a powder in the glove box and triturated with anhydrous hexanes (3×8 mL), decanting the rinsings each time. To the remaining solid was added anhydrous THF (13 mL), and the resulting mixture was re-filtered through a 0.45 μm PTFE syringe filter to remove residual KCl. The filtrate was again concentrated to dryness on the Schlenk line; the resulting solid was crushed to a powder in the glove box and triturated with hexanes (8 mL). Vacuum filtration to afforded 1a as a beige powder (1.30 g, 29.8% yield). $^1$H NMR (400 MHz, toluene-d$^8$): δ 7.07 (s, 4H), 3.09 (s, 4H), 2.00 (s, 12H). $^{13}$C NMR (100 MHz, toluene-d$^8$): δ 244.45, 140.82, 138.79, 131.53, 120.75, 50.38, 17.87 ppm.

1,3-bis(4-chloro-2,6-dimethylphenyl)-4,5-dihydroimidazol-2-ylidene 1b

To 383.7 mg (1.000 mmol) of imidazolium salt 1b HCl in a 20-mL scintillation vial in the glove box was added 4 mL anhydrous toluene followed by 1.00 mL of 1.0 M KHMDS solution in THF (1.0 mmol, 1.0 equiv). The vial was closed and the mixture was agitated for 5-10 min until all of the 1b HCl had gone into solution, with concomitant formation of suspended fine KCl particulates. The reaction mixture was filtered through a 0.45 μm PTFE syringe filter. The solution was concentrated to dryness on the Schlenk line. The resulting white crystalline solid was triturated in the glove box with anhydrous hexanes (3×2 mL) while carrying out vacuum filtration over a medium-porosity frit. Drying under vacuum afforded 1b as a white crystalline solid (267 mg, 76.9% yield). $^1$H NMR (400 MHz, toluene-d$^8$): δ 6.92 (s, 4H), 3.10 (s, 4H), 2.02 (s, 12H). $^{13}$C NMR (100 MHz, toluene-d$^8$): δ 244.66, 140.36, 138.45, 132.49, 128.56, 50.45, 17.96 ppm.

1,3-bis(4-fluoro-2,6-dimethylphenyl)-4,5-dihydroimidazol-2-ylidene 1c was prepared following the identical protocol as for 1b, except reduced in scale by ½ and using 1c HCl in place of 1b HCl as the starting material. 1b was isolated as a white crystalline solid (119 mg, 75.7% yield). $^1$H NMR (400 MHz, toluene-d$^8$): δ 6.62 (d, $^2J_{1_H-19_F}$=9.0 Hz, 4H), 3.13 (s, 4H), 2.07 (s, 12H). $^{13}$C NMR (100 MHz, toluene-d$^8$): δ 245.00, 161.48 (d, $^1J_{13_C-19_F}$=244 Hz), 138.83 (d, $^3J_{13_C-19_F}$=8.70 Hz), 137.87 (d, $^4J_{13_C-19_F}$=2.87 Hz), 115.01 (d, $^2J_{13_C-19_F}$=21.8 Hz), 50.62, 18.19 (d, $^4J_{13_C-19_F}$=1.52 Hz).

$^{19}$F NMR (376.5 MHz, toluene-d$^8$): δ −116.22 (t, $^2J_{19_F-1_H}$=9.0 Hz) ppm.

1,3-bis(4-bromo-2,6-dimethylphenyl)-4,5-dihydroimidazolium-2-(N,N-bis(4-bromo-2,6-dimethylphenyl)amidinate) 2a To 1a (48 mg, 0.11 mmol) in a 0.5-2.0 mL Biotage® microwave vial was added 0.50 mL anhydrous toluene. The vial was crimped and the reaction mixture was heated at 110° C. in an oil bath for 26 hours, during the course of which time the solution became dark yellow, and crystallization of product was observed. The silicone oil was rinsed off from the exterior of the vial with dichloromethane, and the reaction mixture was maintained at room temperature overnight. In the glove box, the mother liquor was separated from the crystals via syringe, and the crystals were rinsed with anhydrous toluene (2×0.3 mL). The crystals were dried on the Schlenk line as well, affording 2a as a crystalline yellow solid (24.3 mg, 58% yield*). $^1$H NMR (400 MHz, CD$_2$Cl$_2$): δ 7.31 (s, 4H), 6.42 (s, 4H), 4.28 (s, 4H), 2.62 (s, 12H), 1.35 (s, 12H). $^{13}$C NMR (100 MHz, CD$_2$Cl$_2$): δ 165.47, 147.64, 139.93, 137.82, 134.26, 132.14, 130.91, 128.74, 123.80, 111.07, 49.55, 19.09, 18.56 ppm. FT-ICR-ESI HRMS: calcd. for C$_{36}$H$_{36}$Br$_4$N$_4$ [M+H]$^+$, most abundant m/z=844.9721; found, 844.9713. FT-IR-ATR: 3037.4 (w), 2966.3 (w), 2910.7 (w), 1576.8 (m), 1544.7 (s), 1528.9 (s), 1464.2 (m, br), 1321.0 (s), 1290.4 (m), 1030.4 (w), 1000.2 (w), 871.3 (m), 856.0 (s), 838.0 (m), 743.1 (m), 693.7 (m) cm$^{-1}$. Dec. pt. 256° C. (indicated by color change to dark orange/brown and confirmed by LC-MS), followed by melting at 258° C. accompanied by evolution of gas.

1,3-bis(4-chloro-2,6-dimethylphenyl)-4,5-dihydroimidazolium-2-(N,N-bis(4-chloro-2,6-dimethylphenyl)amidinate) 2b was prepared following the identical protocol as for 2a, except using 1b (35 mg 0.10 mmol) as the starting material. Product was obtained as a crystalline yellow solid (18.4 mg, 55% yield*). $^1$H NMR (400 MHz, CD$_2$Cl$_2$): δ 7.15 (s, 4H), 6.28 (s, 4H), 4.28 (s, 4H), 2.63 (s, 12H), 1.36 (s, 12H). $^{13}$C NMR (100 MHz, CD$_2$Cl$_2$): δ 165.56, 147.21, 139.72, 138.04, 135.53, 133.76, 130.44, 129.14, 125.84, 123.21, 49.60, 19.17, 18.68 ppm. FT-ICR-ESI HRMS: calcd. for C$_{36}$H$_{36}$Cl$_4$N$_4$ [M+H]$^+$, most abundant m/z=667.1754; found, 667.1768. FT-IR-ATR: 3046.9 (w), 2914.1 (w), 1584.2 (m), 1546.3 (s), 1530.0 (s), 1466.8 (m, br), 1322.1 (m), 1292.7 (m), 1024.8 (w), 1000.4 (w), 877.6 (m), 854.1 (s), 838.9 (m), 744.1 (w), 699.9 (w) cm$^{-1}$. Dec. pt. 250° C. (indicated by color change to dark orange/brown), followed by melting at 255° C. accompanied by evolution of gas.

1,3-bis(4-fluoro-2,6-dimethylphenyl)-4,5-dihydroimidazolium-2-(N,N-bis(4-fluoro-2,6-dimethylphenyl)amidinate) 2c was prepared following the identical protocol as for 2a, except using 1c (31 mg 0.10 mmol) as the starting material. Product was obtained as a crystalline yellow solid (11.5 mg, 38% yield*). $^1$H NMR (400 MHz, CD$_2$Cl$_2$): δ 6.87 (d, $^2J_{1_H-19_F}$=9.0 Hz, 4H), 6.01 (d, $^2J_{1_H-19_F}$=9.6 Hz, 4H), 4.27 (s, 4H), 2.67 (s, 12H), 1.37 (s, 12H). $^{13}$C NMR (100 MHz, CD$_2$Cl$_2$): δ 165.77, 163.08 (d, $^1J_{13_C-19_F}$=248 Hz), 156.69 (d, $^1J_{13_C-19_F}$=234 Hz), 144.73 (d, $^4J_{13_C-19_F}$=2.24 Hz), 140.52 (d, $^3J_{13_C-19_F}$=9.42 Hz), 138.71, 131.29 (d, $^4J_{13_C-19_F}$=2.83 Hz), 130.02 (d, $^3J_{13_C-19_F}$=7.57 Hz), 115.78 (d, $^2J_{13_C-19_F}$=22.5 Hz), 112.10 (d, $^2J_{13_C-19_F}$=20.9 Hz), 49.62, 19.46 (d, $^4J_{13_C-19_F}$=1.48 Hz), 19.01 (d, $^4J_{13_C-19_F}$=1.21 Hz). $^{19}$F NMR (376.5 MHz, CD$_2$Cl$_2$): δ −113.20 (t, $^2J_{19_F-1_H}$=9.0 Hz), −128.87

(t, $^2J_{19_F-1_H}$=9.6 Hz) ppm. FT-ICR-ESI HRMS: calcd. for $C_{36}H_{36}F_4N_4$ [M+H]$^+$, most abundant m/z=601.2949; found, 601.2924. FT-IR-ATR: 3056.4 (w), 2947.3 (w), 2909.5 (w), 1548.8 (m, br), 1478.5 (m, br), 1287.1 (s), 1129.7 (m), 1118.7 (m), 1022.7 (m, br), 854.0 (s), 740.0 (w), 698.3 (w) cm$^{-1}$. Dec. pt. 252° C. (indicated by color change to dark orange/brown), followed by melting at 257-258° C. accompanied by evolution of gas.

1,3-bis(2,4,6-trimethylphenyl)-4,5-dihydroimidazolium-2-(N,N-bis(2,4,6-trimethylphenyl)amidinate) SICDI was prepared following the identical protocol as for 2a, except using SIMes (31 mg 0.10 mmol) as the starting material. No crystallization was observed during the course of the reaction, so the product was obtained after concentration, rinsing with hexanes, and drying as one batch: a mixture of powdery dark-yellow and crystalline yellow solids (crystalline phase formed during the course of concentration) (14.6 mg, 50% yield**). $^1$H NMR (400 MHz, $CD_2Cl_2$): δ 6.93 (s, 4H), 6.07 (s, 4H), 4.23 (s, 4H), 2.63 (s, 12H), 2.28 (s, 6H), 1.90 (s, 6H), 1.34 (s, 12H). $^{13}$C NMR (100 MHz, $CD_2Cl_2$): δ 165.67, 146.49, 139.78, 138.09, 137.39, 133.02, 129.68, 128.61, 126.91, 126.83, 49.55, 21.14, 20.40, 19.23, 18.61 ppm. FT-ICR-ESI HRMS: calcd. for $C_{36}H_{36}Cl_4N_4$ [M+H]$^+$, most abundant m/z=585.3952; found, 585.3932. FT-IR-ATR: 3023.2 (w, shoulder), 2914.1 (w), 1543.5 (s), 1480.2 (m, br), 1322.0 (m, br), 1280.5 (m), 1034.0 (w, br), 848.0 (m), 709.9 (w) cm$^{-1}$. Dec. pt. 211-215° C. (indicated by color change to dark orange/brown) with concomitant melting and evolution of gas.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A compound comprising the structure:

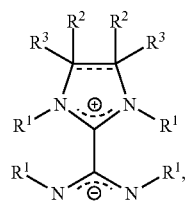

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile, provided at least two $R^1$ are optionally substituted aryl;
each $R^2$ and $R^3$ are the same or different and are absent, hydrogen, optionally substituted alkyl, optionally substituted heteroalkyl, halo, optionally substituted acyl, or optionally substituted phosphine;
⁓⁓⁓ is a single or double bond, provided when ⁓⁓⁓ is a double bond, each $R^3$ is absent.

2. A compound as in claim 1, wherein each $R^1$ is the same or different and are hydrogen, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile, provided at least two $R^1$ are optionally substituted aryl.

3. A compound as in claim 1, wherein each $R^1$ is the same or different and are optionally substituted cycloalkyl, optionally substituted cycloheteroalkyl, optionally substituted cycloalkenyl, optionally substituted aryl, or optionally substituted heteroaryl, provided at least two $R^1$ are optionally substituted aryl.

4. A compound as in claim 1, wherein the compound has the structure:

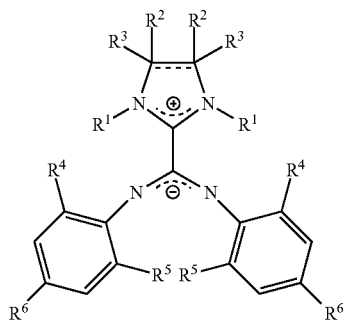

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile;
each $R^2$ and $R^3$ are the same or different and are absent, hydrogen, optionally substituted alkyl, optionally substituted heteroalkyl, halo, optionally substituted acyl, or optionally substituted phosphine;
each $R^4$, $R^5$, and $R^6$ are same or different and are hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocyanate, or nitrile; and
⁓⁓⁓ is a single or double bond, provided when ⁓⁓⁓ is a double bond, each $R^3$ is absent.

5. A compound as in claim 1, wherein each $R^1$ is the same or different and comprises the structure:

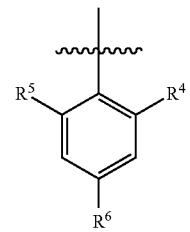

wherein each $R^4$, $R^5$, and $R^6$ are same or different and are hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocyanate, or nitrile.

6. A compound as in claim 4, wherein each $R^4$, $R^5$, and $R^6$ are the same or different and are halide, optionally substituted alkyl, or optionally substituted aryl.

7. A compound as in claim 4, wherein each $R^4$, $R^5$, and $R^6$ are the same or different and are halide or optionally substituted alkyl.

8. A compound as in claim 1, wherein ⁓⁓⁓ is a single bond.

9. A compound as in claim 1, wherein:
each $R^1$ comprises the structure:

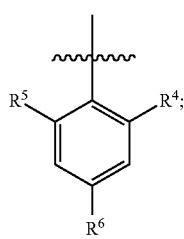

each $R^2$ and $R^3$ are hydrogen, optionally substituted alkyl, optionally substituted heteroalkyl, halo, optionally substituted acyl, or optionally substituted phosphine;

each $R^4$, $R^5$, and $R^6$ are same or different and are hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocyanate, or nitrile; and ----- is a single bond.

10. A compound as in claim 1, wherein:
each $R^1$ comprises the structure:

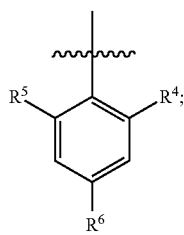

each $R^2$ and $R^3$ are hydrogen, optionally substituted alkyl, or optionally substituted heteroalkyl;

each $R^4$ and $R^5$ are optionally substituted alkyl;

$R^6$ is halo; and

----- is a single bond.

11. A compound as in claim 1, wherein each $R^2$ and $R^3$ are hydrogen or optionally substituted alkyl.

12. A compound as in claim 1, wherein $R^2$ and $R^3$ are hydrogen.

13. A method, comprising:
forming a compound of claim 1 by heating a precursor compound to a temperature of about 80° C. or greater, wherein the percent conversion to the compound is greater than or equal to 50%, and wherein the precursor compound has the structure:

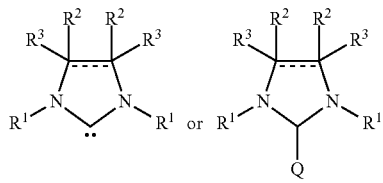

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile, provided at least two $R^1$ are optionally substituted aryl;

each $R^2$ and $R^3$ are the same or different and are absent, hydrogen, optionally substituted alkyl, optionally substituted heteroalkyl, halo, optionally substituted acyl, or optionally substituted phosphine;

----- is a single or double bond, provided when ----- is a double bond, each $R^3$ is absent; and Q is a thermolabile or photolabile protecting group.

14. A method for forming a compound comprising the structure:

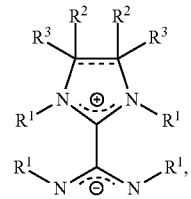

or a tautomer thereof, wherein the method comprises the step of heating a precursor compound to a temperature of about 80° C. or greater, wherein the percent conversion to the compound is greater than or equal to 50%, and wherein the precursor compound has the structure:

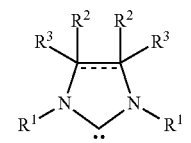

or a tautomer thereof, wherein:
each $R^1$ is the same or different and are hydrogen, optionally substituted alkyl, alcohol, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, optionally substituted acyl, optionally substituted amino, optionally substituted phosphine, or nitrile, provided at least two $R^1$ are optionally substituted aryl;

each $R^2$ and $R^3$ are the same or different and are absent, hydrogen, optionally substituted alkyl, optionally substituted heteroalkyl, halo, optionally substituted acyl, or optionally substituted phosphine; and ----- is a single or double bond, provided when ----- is a double bond, each $R^3$ is absent.

15. A method as in claim 14, comprising heating the precursor compound to a temperature greater than or equal to about 100° C.

16. A method as in claim 14, comprising heating the precursor compound to a temperature between about 80° C. and about 130° C.

17. A method as in claim 14, comprising heating the precursor compound for greater than or equal to about 6 hours.

18. A method as in claim 14, wherein the percent conversion is greater than or equal to about 70%.

* * * * *